US009486147B2

(12) United States Patent
Jung et al.

(10) Patent No.: US 9,486,147 B2
(45) Date of Patent: Nov. 8, 2016

(54) METHOD FOR CONTROLLING A SPIROERGOMETRIC SYSTEM AND SPIROERGOMETRIC SYSTEM

(75) Inventors: Gunnar Jung, Furth (DE); Dirk Tuchtenhagen, Furth (DE); Markus Schotters, Dresden (DE); Martin Kusch, Dormagen (DE)

(73) Assignee: ACEOS GMBH, Furth (DE)

( * ) Notice: Subject to any disclaimer, the term of this patent is extended or adjusted under 35 U.S.C. 154(b) by 1132 days.

(21) Appl. No.: 13/390,257

(22) PCT Filed: Aug. 5, 2010

(86) PCT No.: PCT/EP2010/004805
§ 371 (c)(1),
(2), (4) Date: Apr. 30, 2012

(87) PCT Pub. No.: WO2011/018187
PCT Pub. Date: Feb. 17, 2011

(65) Prior Publication Data
US 2012/0209128 A1 Aug. 16, 2012

(30) Foreign Application Priority Data

Aug. 13, 2009 (DE) .................. 10 2009 037 038
Sep. 16, 2009 (DE) .................. 10 2009 041 425

(51) Int. Cl.
*A61B 5/08* (2006.01)
*A61B 5/0205* (2006.01)
(Continued)

(52) U.S. Cl.
CPC ............. *A61B 5/0205* (2013.01); *A61B 5/083* (2013.01); *A61B 5/222* (2013.01); *A63B 23/18* (2013.01);
(Continued)

(58) Field of Classification Search
CPC combination set(s) only.
See application file for complete search history.

(56) References Cited

U.S. PATENT DOCUMENTS 6,302,103 B1   10/2001   Resnick
6,387,053 B1 *  5/2002   Pessenhofer ........... A61B 5/083
                                                        600/529
(Continued)

FOREIGN PATENT DOCUMENTS

EP    1825888 A1   8/2007
GB    2162642 A    2/1986
(Continued)

OTHER PUBLICATIONS

Rhodes, Jonathan, et al. "Excessive Anaerobic Metabolism During Exercise After Repair of Aortic Coarctation." The Journal of pediatrics 131.2 (1997): 210-214.*
(Continued)

*Primary Examiner* — Michael Kahelin
*Assistant Examiner* — Mitchell E Alter
(74) *Attorney, Agent, or Firm* — Jason H. Vick; Sheridan Ross, PC

(57) ABSTRACT

Shown and described is a method for controlling and/or regulating a spiroergometry system (1) for determining energy metabolism during physical exertion, wherein the spiroergometry system (1) has a user unit (2) arranged in the flow of the inhaled and exhaled air of a test subject (4) for removing a respiratory gas sample of the test subject (4), at least one analysis unit (5) for measuring the respiratory gas composition and/or the respiratory flow volume and for determining physiological parameters relating to the ventilation and/or gas exchange of the test subject (4), particularly for determining the oxygen volume taken in during at least one inhalation of the test subject (4) and the carbon dioxide volume exhaled after the breath and, preferably, the respiratory quotient, at least one measuring device (6) for measuring the heart rate of the test subject (4), at least one control device (7) for controlling the spiroergometry system (1) and a cardio equipment unit (8) for the physical exertion of the test subject (4), wherein as the exertion of the test subject increases incrementally during use of the cardio equipment unit (8), a measurement of the respiratory gas composition and/or respiratory flow volume is performed automatically only toward the end of an exertion stage or of a performance stage prior to an increase in exertion, and a determination is made of the physiological parameters, particularly a determination of the inhaled oxygen volume and of the exhaled carbon dioxide volume with respect to at least one breath toward the end of the exertion stage.

9 Claims, 1 Drawing Sheet

(51) Int. Cl.
*A61B 5/083* (2006.01)
*A61B 5/22* (2006.01)
*A63B 23/18* (2006.01)
*A61B 5/024* (2006.01)
*A61B 5/091* (2006.01)
*A63B 24/00* (2006.01)

(52) U.S. Cl.
CPC .............. *A61B 5/024* (2013.01); *A61B 5/0833* (2013.01); *A61B 5/0836* (2013.01); *A61B 5/091* (2013.01); *A63B 24/0087* (2013.01); *A63B 2230/433* (2013.01); *A63B 2230/436* (2013.01)

(56) References Cited

U.S. PATENT DOCUMENTS

| | | | | |
|---|---|---|---|---|
| 2003/0013072 | A1* | 1/2003 | Thomas | 434/247 |
| 2003/0023182 | A1* | 1/2003 | Mault | A61B 5/083 600/532 |
| 2003/0183227 | A1 | 10/2003 | Klemperer | |
| 2004/0186389 | A1* | 9/2004 | Mault | A61B 5/0833 600/531 |
| 2004/0186390 | A1* | 9/2004 | Ross | A61B 5/083 600/532 |
| 2008/0149105 | A1 | 6/2008 | Matula et al. | |
| 2008/0200824 | A1* | 8/2008 | Kane et al. | 600/532 |
| 2011/0004113 | A1 | 1/2011 | Jerichow | |
| 2011/0105281 | A1 | 5/2011 | Jerichow | |

FOREIGN PATENT DOCUMENTS

| | | |
|---|---|---|
| WO | WO 2009/024427 | 2/2009 |
| WO | WO 2009/024427 A1 | 2/2009 |
| WO | WO 2009/056457 | 5/2009 |
| WO | WO 2009/056457 A1 | 5/2009 |

OTHER PUBLICATIONS

International Search Report prepared by the European Patent Office on Nov. 8, 2010, for International Application No. PCT/EP2010/004805.

Written Opinion for PCT Patent Application No. PCT/EP2010/004805, mailed Nov. 8, 2010.

International Preliminary Report on Patentability for PCT Patent Application No. PCT/EP2010/004805, mailed Feb. 14, 2012.

* cited by examiner

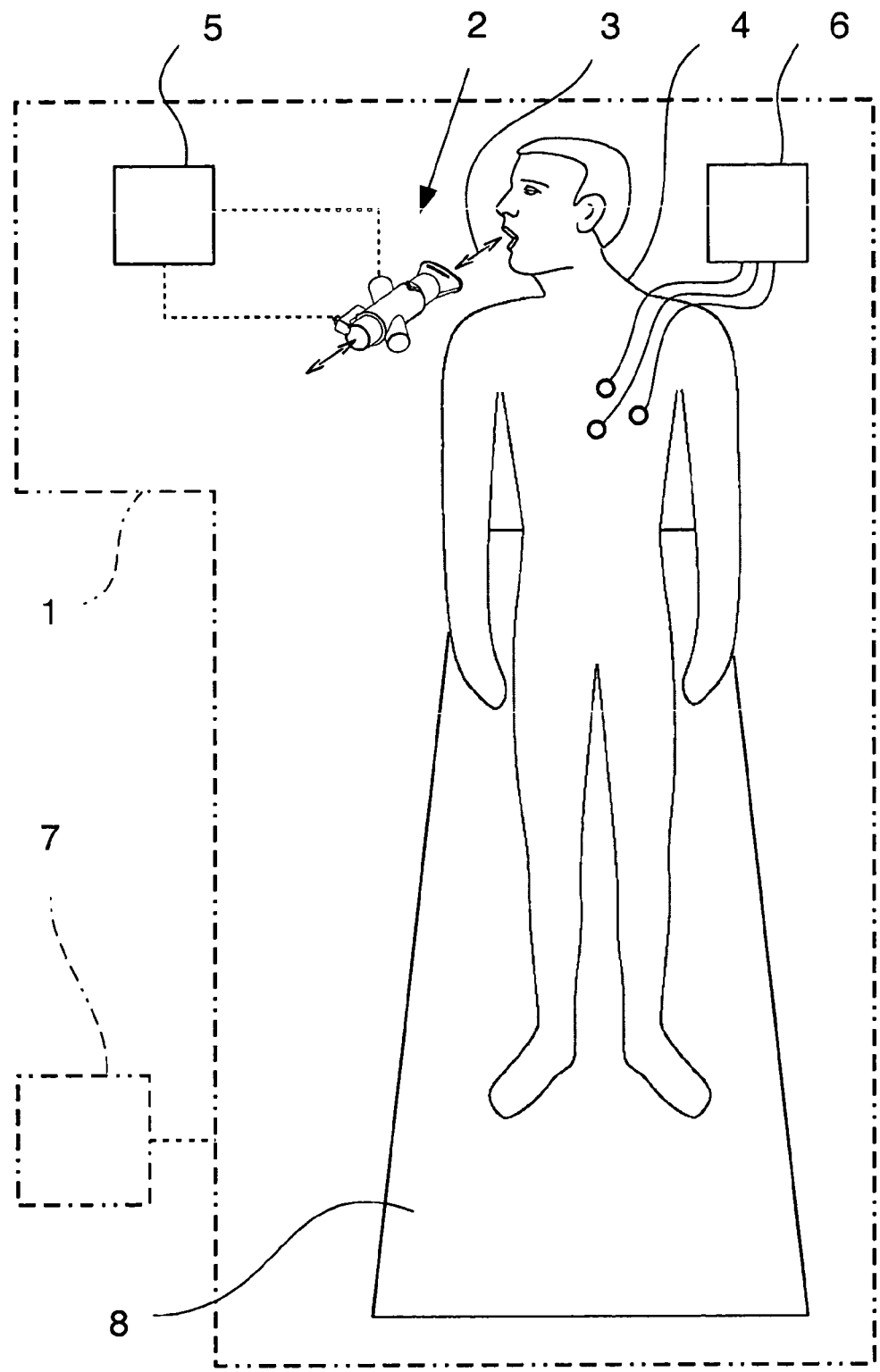

METHOD FOR CONTROLLING A SPIROERGOMETRIC SYSTEM AND SPIROERGOMETRIC SYSTEM

CROSS REFERENCE TO RELATED APPLICATIONS

This application is a national stage application under 35 U.S.C. 371 of PCT Application No. PCT/EP2010/004805 having an international filing date of 5 Aug. 2010, which designated the United States, which PCT application claimed the benefit of German Application No. 10 2009 037 038.2 filed Aug. 13, 2009, and German Application No. 10 2009 041 425.8 filed Sep. 16, 2009, the entire disclosure of each of which is incorporated herein by reference.

The invention relates to a method for controlling a spiroergometry system for determining the energy metabolism during physical exertion and a commensurately designed spiroergometry system.

In classic spiroergometry, a test subject's respiratory gases are measured during physical exertion. The most important respiratory gas parameters that are detected during spiroergometry are oxygen uptake, carbon dioxide exhaled, respiratory minute volume and respiratory rate. Additional parameters can be calculated from these, such as the respiratory quotient, the respiratory equivalent for oxygen and/or for $CO_2$, and the tidal volume.

With the aid of parameters such as, for example, the maximum oxygen uptake during increasing physical exertion and the aerobic and anaerobic threshold, meaningful conclusions can be drawn regarding a test subject's endurance.

Based on the stoichiometric relationships between gas exchange (oxygen consumption, carbon dioxide production) and substrate metabolism, the respective substrate oxidation rates of the carbohydrate oxidation and the lipid oxidation can be determined on the basis of the determined quantity of the oxygen taken in during an inhalation and the quantity of carbon dioxide subsequently exhaled. These relationships are known to those skilled in the art as indirect calorimetry. Spiroergometry can therefore be used to measure the energy metabolism during physical exertion in order to determining the test subject's calorie consumption and substrate conversion (fat and carbohydrate metabolism). Moreover, through comparison to standard values from the results of spiroergometry, conclusions can be drawn regarding the functional capacity of the test subject's cardiopulmonary system.

Maximum oxygen uptake is regarded as a classic parameter for assessing endurance. The parameter of maximum oxygen uptake is also used in order to establish individual training intensities. Here, standard percent ranges are used as a kind of filter which is placed over individually measured values for maximum oxygen uptake in order to establish an "individual" basic training range. This leads to generalization and to imprecise training recommendations. For example, taking statistical values into account, the basic training range of humans is always around 65% of the maximum oxygen uptake, which by no means describes the actual individual basic training range and does not allow for a targeted training recommendation. When determining the maximum oxygen uptake, the test subject is worked to full exertion. The maximum oxygen uptake is independent here from the ventilation, the cardiovascular capacity and the local oxygen exhaustion in the muscles. The test subject must therefore be capable of exerting himself to complete exhaustion. However, certain clinical pictures rule out maximum exertion from the outset.

In methods known from the prior art for respiratory gas measurement using a spiroergometry device, it is necessary for the test subject to wear a face mask during the measurement to which a volume flow sensor for measuring the air volume as well as a thin hose acting as an extraction line are connected. A gas sample is removed from the exhaled air through the hose and fed to gas sensors in order to determine the concentrations of the gas components. The proportional gas content of the exhaled air is then compared to the ambient air. The calculation of absolute values is possible if the ventilated air volume is known. Physiological parameters of the test subject's energy metabolism are then determined on the basis of the measured values. These processes and corresponding sensors for respiratory gas analysis are in principle already known to those skilled in the art.

Since the respiratory gas composition and the respiratory flow volume are measured continuously to determine the maximum oxygen uptake, it is necessary for the test subject to wear the face mask for the entire 8- to 30-minute duration of the test, which is generally perceived as a nuisance. Moreover, the long test duration until a maximum exertion is reached in order to determine the maximum oxygen uptake is disadvantageous and very strenuous for the test subject.

A method for controlling and/or regulating a training or rehabilitation unit is known from WO 2009/056457 A1, wherein respiratory gas compositions and/or respiratory flow volumes are measured with the aid of a sensor unit on the basis of which a test subject's physiological parameters of ventilation and/or gas exchange can be determined. A provision is made in the known method for the continuous determination of performance characteristics on the basis of the determined physiological parameters at submaximum exertion with the aid of a regression function and/or through exertion up to maximum capacity. Another method for controlling and/or regulating a training and/or rehabilitation unit is known from WO 2009/024427 A1.

It is the object of the present invention to provide a method for controlling a spiroergometry system and a spiroergometry system, each of the type mentioned at the outset with which an individual performance and metabolic diagnosis, particularly the creation of targeted individual nutritional, exercise and training instructions, is achieved easily and with a high level of precision. Moreover, the intention is to make individual performance and metabolic diagnosis possible over a shorter test duration and with a higher level of comfort for the test subject, the test subject's physical exertion being kept to a minimum.

To achieve the abovementioned objects, a method for controlling a spiroergometry system for determining the energy metabolism during physical exertion is proposed according to the invention, wherein the spiroergometry system has a user unit arranged in the flow of a test subject's inhaled and exhaled air for removing a test subject's respiratory gas sample, at least one analysis unit for measuring the respiratory gas composition and/or the respiratory flow volume and for determining physiological parameters relating to the test subject's ventilation and/or gas exchange, particularly for determining the oxygen volume taken in during at least one inhalation of the test subject and the carbon dioxide volume exhaled after the breath and, preferably, the respiratory quotient, at least one measuring device for measuring the test subject's heart rate, at least one control device for controlling the spiroergometry system and a cardio equipment unit for the physical exertion of the test subject, wherein as the exertion of the test subject increases incrementally, i.e., as the exercise performed by the test subject on the cardio equipment unit is increased incrementally, a preferably automatic measurement of the respiratory gas composition and/or respiratory flow volume is performed only toward the (temporal) end of an exertion stage or of a performance stage prior to an increase in exertion and a determination is made of the physiological parameters on the basis of the measured values, particularly a determination of the inhaled oxygen volume and of the exhaled carbon dioxide volume with respect to at least one breath toward the end of the exertion stage. Accordingly, the spiroergometry system according to the invention has a control device which is designed to execute the aforementioned method.

Unlike the prior art, the method according to the invention provides not for a continuous, but for a discontinuous determination of the physiological parameters of ventilation and/or gas exchange, particularly the determination of the inhaled oxygen volume and the exhaled carbon dioxide volume. Based on the determined physiological parameters, a truly individual performance and metabolic diagnosis is then possible, the test subject being preferably subjected to increasing exertion over a plurality of exertion stages starting from a resting state to a state of high exertion in which the anaerobic threshold is reached or has already been exceeded. By determining the physiological parameters only at the end of each exertion stage, with each exertion stage preferably extending over an equal time period, the number of required measurements is reduced and a precise determination of the energy metabolism profile under increasing exertion is achieved at the same time. This contributes to a high level of user comfort and shortens the overall duration of the energy metabolism diagnosis.

The method according to the invention and the spiroergometry system according to the invention enable the determination of a personal energy metabolism, i.e., of the individual preparation of fats and carbohydrates for energy production in the muscles. As a result, targeted individual nutritional, exercise and training instructions can be created. According to the invention, at a certain point in time and over a short period, the quantity of inhaled and exhaled oxygen and carbon dioxide are particularly determined. In doing so, the goal can be to determine the exertion intensity at which the optimum aerobic, i.e., oxygenbased, fat metabolism is achieved, for example. It is at this point that a maximum proportion of energy is produced through the burning of fat in the body. By training in this exertion range, the ability of the organism to make energy available from fats is improved. To control the intensity of the training, the user then orients himself to the heart rate that was measured at the same time as the determined optimal burning of fat. Preferably, the exertion intensity at which the anaerobic threshold is reached can be determined automatically.

The method according to the invention and the corresponding spiroergometry system offer the advantage that the full exertion of the test subject is not absolutely necessary during the determination of the individual energy metabolism profile. When using the method according to the invention, the energy metabolism profile is not calculated working backward from the maximum oxygen uptake, but rather actually measured (discontinuously) during the preferably submaximum exertion of the test subject. As a result, a high level of precision is ensured during the detection of the personal energy metabolism without the need for performing a statistical estimation.

Moreover, as a result of the discontinuous measurement only toward the end of an exertion stage, it is not necessary for the test subject to wear a breathing mask or the like for the entire duration of an exertion stage. In particular, on the basis of spot measurements at the end of the exertion stages, such user units can be used which consist of a device housing and a (replaceable) breathing tube with an extraction point for the removal of respiratory gas, wherein a provision can be made to seal the nose in order to exclude nasal breathing on the part of the test subject when a gas sample is removed from the user unit.

The wearing of a face mask is no longer necessary at all when using user units of the above-described type, which results in a high level of test comfort for the subject.

As a result, the method according to the invention and the spiroergometry system according to the invention enable a very quick, simple and precise determination of the individual actual state of the energy metabolism of a test subject with a relatively low number of measurements.

In the method according to the invention, oxygen uptake, carbon dioxide exhaled and/or parameters derived therefrom such as the anaerobic threshold, the respiratory quotient and/or the oxygen pulse are preferably determined as parameters of gas exchange. The tidal volume, respiratory rate and respiratory time volume and/or the respiratory equivalent for oxygen derived therefrom can be preferably determined as parameters of ventilation.

A cardio equipment unit in terms of the invention can be an ergometer, a fitness machine, a cross-trainer, a rowing ergometer, a rowing machine, a treadmill, a walking machine, a stationary bicycle, or a bicycle or the like.

In order to determine the personal energy metabolism profile under increasing exertion, is may already be sufficient to provide for the measurement of the respiratory gas composition and/or the respiratory flow volume and the determination of the physiological parameters automatically over a time period of less than 40 seconds, preferably less than 30 seconds, particularly less than 10 to 20 seconds, prior to the end of an exertion stage. The physiological parameters can be determined automatically preferably for the last five or for fewer than five breaths prior to the end of an exertion stage. However, the measurement of the respiratory gas composition and/or respiratory flow volume to determine the desired physiological parameters should only be performed once the energy metabolism has reached a stable or unchanging state. With a stable energy metabolism state and unchanging exertion on the part of the test subject, even one breath could be sufficient to determine the desired physiological parameters with a high degree of precision for the respective exertion range. Consequently, the method according to the invention makes it possible to provide very exact information on the test subject's energy metabolism with a small number of measurements.

To ensure a short total duration of the determination of the energy metabolism profile as a function of the test subject's exertion, the duration of an exertion stage can be less than 3 minutes, preferably approximately 2 minutes or even less. The increase in exertion between two adjacent exertion stages can be between 10 watts to 100 watts, preferably about 25 watts, ensuring an exact determination of the energy metabolism profile as a function of the exertion of the test subject when using the cardio equipment unit. In this connection, it has been found that a stable metabolic state can set in, for example, after a period of more than 60 seconds, preferably more than 75 seconds, particularly after about 90 seconds, so that the measurement of the respiratory gas composition and/or respiratory flow volume and the determination of the physiological parameters can then be performed.

In the measurement period prior to the end of the respective exertion stage, the physiological parameters for each breath in the measurement period can be determined individually and then the averages of the determined physiological parameters over the total number of breaths taken in the measurement period prior to the end of the exertion stage can be found automatically. This contributes to a high level of precision in the determination of the energy metabolism parameters. Moreover, a provision can be made that faulty breaths are recognized automatically and excluded from the averaging. A "faulty" breath can be determined, for example, from a deviation in the curve profile of the measured oxygen and/or carbon dioxide concentration and/or in the measured respiratory volume flow from an expected curve profile.

A performance unit of the cardio equipment unit which determines the exertion of the test subject, for example a resistance or braking arrangement of the cardio equipment unit, can be controlled and/or regulated manually or, preferably, automatically or, also preferably, as a function of previously determined physiological parameters.

To determine the exertion intensity at which optimal fat metabolism is reached, full exertion on the part of the test subject is not absolutely necessary. According to the invention, the determination of the physiological parameters can be performed in this context only in exertion stages which lead to a respiratory quotient of no more than about 1.1, preferably about 1.0. The determination of the maximum oxygen uptake upon full exertion of the test subject is then not provided for. As a result, both the total duration of the analysis of the energy metabolism and the physical demands on the test subject are reduced considerably.

In principle, however, it is also possible for a stepwise increase in exertion to be provided for until a respiratory quotient of less than 1.09, preferably of about 1.0, is reached and the physiological parameters to be determined toward the end of the respective exertion stage, and for the exertion to then be increased in a continuous manner until a greater respiratory quotient is reached and to continuously determine the physiological parameters. In this embodiment of the method according to the invention, the individual performance and metabolic diagnostics relating to the determination of the energy metabolism parameters under suboptimum exertion on the basis of a ramp test with a stepped increase of the exertion and discontinuous measurement include the subsequent determination of the maximum oxygen uptake under full exertion of the test subject and preferably continuous measurement. This enables a very extensive performance diagnosis of the test subject's energy metabolism.

In contrast, in an alternative embodiment, a provision is made that the exertion of the test subject is increased in steps and the physiological parameters are determined toward the end of the respective exertion stage, particularly until a respiratory quotient of about 1.1, preferably 1.0, is reached. As a result, a stepwise increase of the exertion of the test subject can be performed until the test subject's maximum functional capacity at full exertion is reached. For a high degree of precision in the determination of the maximum oxygen uptake in connection with the assessment of endurance, the step height, i.e., the increase in exertion from one exertion stage to the next, or the time interval of the increase can be increased accordingly once a respiratory quotient of about 1.0, preferably of about 1.09, is reached, and/or the time interval from one increase to the next can be reduced.

The following table shows an example of the measured values for a test subject's energy metabolism under different exertion levels. The measurement of the respiratory gas composition and/or the respiratory flow volume and the determination of the physiological parameters "oxygen uptake," "carbon dioxide exhaled" and "respiratory quotient RER" and, derived from this, the information on calorie consumption refer to a measurement period of no more than 30 s prior to the end of the respective exertion stage.

TABLE 1

Energy metabolism profile under increasing exertion of the test subject

| Stage | Output [watts] | Duration | RER [ ] | Fat [kCal/h] | Carb. [kCal/h] | % fat [%] | % carb. [%] | HR [1/min] | Energy [kCal/h] |
|---|---|---|---|---|---|---|---|---|---|
| Resting | 0.0 | 00:00:57 | 0.85 | 121 | 117 | 50 | 50 | 72 | 231 |
| 1 | 75.0 | 00:02:01 | 0.81 | 242 | 139 | 63 | 37 | 80 | 383 |
| 2 | 125.0 | 00:02:00 | 0.85 | 273 | 242 | 51 | 49 | 95 | 546 |
| 3 | 175.0 | 00:01:59 | 0.86 | 300 | 352 | 46 | 54 | 105 | 655 |
| 4 | 225.0 | 00:02:01 | 0.89 | 299 | 509 | 37 | 63 | 121 | 814 |
| 5 | 275.0 | 00:01:58 | 0.91 | 291 | 687 | 30 | 70 | 134 | 979 |
| 6 | 325.0 | 00:01:59 | 0.96 | 168 | 967 | 15 | 85 | 145 | 1144 |
| 7 | 375.0 | 00:02:01 | 1.03 | 0 | 1339 | 0 | 100 | 157 | 1339 |
| 8 | 425.0 | 00:02:00 | 1.07 | 0 | 1476 | 0 | 100 | 165 | 1476 |
| 9 | 475.0 | 00:01:58 | 1.06 | 0 | 1447 | 0 | 100 | 167 | 1447 |

According to Table 1, the test subject has a very good basic endurance. As concerns the fat metabolism ranges, the regenerative training range up to a pulse of about 102 can be seen at 140 watts, along with the extensive basic range up to a pulse of about 134 at 275 watts. Intensive training occurs at a heart rate of 134 to 152 (275 to 350 watts). Very intensive training in the transitional range to anaerobic energy production should occur over a heart rate of 152 at more than 350 watts. The maximum heart rate is about 167, which also explains lower training heart rates.

Based on the physiological parameter values calculated in Table 1, individual training ranges can be given, as shown below in Table 2.

TABLE 2

Individual training ranges

| | TR1 | TR2 | TR3 | TR4 |
|---|---|---|---|---|
| Heart rate | <108 | 108-134 | 134-153 | >153 |
| Watts | <150 | 150-275 | 275-358 | >358 |

The first training range TR1, "Regeneration," constitutes a range with individual high active fat metabolism (relative proportion of energy production). Range TR2, "Basic training," comprises extensive low-intensity basic training to improve the aerobic metabolism. Individually, there is a high level of fat burning. The third range TR3, "Buildup," includes intensive, higher-intensity basic training for improving the aerobic functional capacity and the functional capacity of the cardiovascular system. It is here that intensive carbohydrate burning begins. The fourth range TR4, "Competition and top-level range," relates to the very intensive training range on the transition to anaerobic energy production, such as in interval training or speed training.

The determined energy metabolism profile can be depicted graphically as a function of exertion intensity. Individual training ranges can be determined either manually or automatically from the measured energy metabolism, particularly from the fat metabolism.

More specifically, there are numerous possibilities for arranging and modifying the method according to the invention, in which respect reference is made to the independent patent claims on the one hand and to the following description of a preferred embodiment of the invention with reference to the drawing on the other hand.

The FIGURE shows a schematic illustration of a method for controlling and/or regulating a spiroergometry system 1 for determining energy metabolism during physical exertion. The spiroergometry system 1 has a user unit 2 for removal of a respiratory gas sample 3 of a test subject 4 arranged in the flow of the inhaled and exhaled air and at least one schematically depicted analysis unit 5 for measuring the respiratory gas composition and/or the respiratory flow volume and for determining physiological parameters of ventilation and/or gas exchange of the test subject 4, particularly for determining the oxygen volume taken up during a breath of the test subject 4 and the carbon dioxide volume exhaled after the breath and, preferably, the respiratory quotient. Moreover, a measuring device 6 for measuring the heart rate of the test subject 4 is provided which is also shown only schematically in the FIGURE. Finally, the spiroergometry system 1 has a control device 7 for controlling the spiroergometry system 1 and a cardio equipment unit 8 for the physical exertion of the test subject 4.

In the depicted method, a measurement of the respiratory gas composition and/or the respiratory flow volume and the determination of the physiological parameters occur preferably automatically under the stepwise increasing exertion of the test subject 4 upon using the cardio equipment unit 8 only toward the end of an exertion stage period prior to an increase in exertion. In particular, the inhaled oxygen volume and the exhaled carbon dioxide volume are determined with respect to at least one breath toward the end of the exertion stage.

Moreover, the control device 7 can be embodied and work together with the spiroergometry system 1 in such a way that a method according to the subclaims can be executed.

The invention claimed is:

1. A method of using a spiroergometry system, comprising:
    removing, using a user unit arranged in a flow of inhaled and exhaled air of a test subject a respiratory gas sample of the test subject;
    measuring, with at least one analysis unit, one or more of:
        a respiratory gas composition and a respiratory flow volume;
    determining an oxygen volume taken in during at least one inhalation of the test subject and a carbon dioxide volume exhaled after the at least one inhalation and a respiratory quotient;
    measuring a heart rate of the test subject; and
    monitoring, by a cardio equipment unit, a physical exertion of the test subject;
    wherein as the exertion of the test subject increases incrementally during the use of the cardio equipment unit, measuring of the one or more of the respiratory gas composition and respiratory flow volume only toward the end of an exertion stage of the test subject prior to an increase in exertion, and a determination is made of the inhaled oxygen volume and of the exhaled carbon dioxide volume with respect to at least one breath toward the end of the exertion stage; and
    an incremental increase in exertion is provided until a respiratory- quotient of less than 1.09 is reached,
    an incremental increase in exertion is provided and physiological parameters are determined discontinuously toward an end of the respective exertion stage,
    measuring discontinuously an oxygen composition and oxygen flow volume from at least one inhalation of the test subject and a carbon dioxide composition and carbon dioxide flow volume from at least one exhalation of the test subject only toward the end of an exertions stage prior to an increase in exertion and prior to the respiratory quotient being 1.09; and
    when a respiratory quotient greater than 1.09 is reached, the exertion level is subsequently increased in a continuous manner and the physiological parameters are determined continuously and oxygen composition and oxygen flow volume from at least one inhalation of the test subject and a carbon dioxide composition and carbon dioxide flow volume from at least one exhalation of the test subject are continuously measured.

2. The method as set forth in claim 1, wherein the measurement of one or more of the respiratory gas composition and the respiratory flow volume, and the determination of the physiological parameters, occurs automatically and discontinuously over a time period of less than 40 seconds prior to an end of the exertion stage.

3. The method as set forth in claim 1, wherein the physiological parameters are determined automatically for less than 8 breaths prior to an end of the exertion stage.

4. The as set forth in claim 1, wherein a duration of an exertion stage is less than 3 minutes.

5. The method as set forth in claim 1, wherein the increase in exertion between two adjacent exertion stages is between 10 watts and 100 watts.

6. The method as set forth in claim 1, wherein the physiological parameters are determined for each breath prior to the end of the exertion stage and the values of the physiological parameters for the entire number of breaths taken in a period of time prior to the end of the exertion stage are averaged automatically.

7. The method as set forth in claim 1, wherein faulty breaths are recognized automatically and excluded from averaging.

8. The method as set forth in claim 1, wherein a performance unit of the cardio equipment unit determining the exertion of the test subject is controlled automatically.

9. The method as set forth in claim 1, wherein until a respiratory quotient of less than or equal to 1.03 is reached, an incremental increase in exertion is provided and the physiological parameters are determined discontinuously toward the end of the respective exertion stage, and that when a greater respiratory quotient than 1.03 is reached, the exertion is subsequently increased in a continuous manner and the physiological parameters are determined continuously.

* * * * *